(12) United States Patent
Wang et al.

(10) Patent No.: US 10,166,211 B1
(45) Date of Patent: *Jan. 1, 2019

(54) NITRIC OXIDE RELEASING COMPOUND, PHARMACEUTICAL COMPOSITION, USE AND SYNTHESIS METHOD THEREOF

(71) Applicant: NATIONAL CHIAO TUNG UNIVERSITY, Hsinchu (TW)

(72) Inventors: Yun-Ming Wang, Kaohsiung (TW); Wen-Feng Liaw, Taichung (TW); Yu-Jen Chen, Kaohsiung (TW); Shou-Cheng Wu, Yilan County (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/879,450

(22) Filed: Jan. 25, 2018

(30) Foreign Application Priority Data

Oct. 24, 2017 (TW) .............................. 106136571 A

(51) Int. Cl.
| | | |
|---|---|---|
| A61K 31/295 | (2006.01) | |
| A61K 9/00 | (2006.01) | |
| A61P 9/10 | (2006.01) | |
| C01B 21/24 | (2006.01) | |
| A61P 5/48 | (2006.01) | |
| A61K 33/26 | (2006.01) | |
| C07F 15/02 | (2006.01) | |

(52) U.S. Cl.
CPC .......... *A61K 31/295* (2013.01); *A61K 9/0019* (2013.01); *A61K 33/26* (2013.01); *A61P 5/48* (2018.01); *A61P 9/10* (2018.01); *C01B 21/24* (2013.01); *C07F 15/025* (2013.01)

(58) Field of Classification Search
CPC ...................................................... C07F 15/025
See application file for complete search history.

(56) References Cited

U.S. PATENT DOCUMENTS

| | | | |
|---|---|---|---|
| 2015/0164845 A1* | 6/2015 | Gorath .................. | A61K 31/21 558/486 |
| 2016/0256522 A1 | 9/2016 | Tai et al. | |
| 2017/0049809 A1 | 2/2017 | Szabo | |
| 2018/0208616 A1* | 7/2018 | Lu ........................ | A61K 31/555 |

FOREIGN PATENT DOCUMENTS

| | | |
|---|---|---|
| TW | I382851 B | 1/2013 |
| TW | 201632199 A | 9/2016 |

OTHER PUBLICATIONS

Cui et al. {FEMS Microbiology Letters (1992), 98(13), pp. 67-70 (Year: 1992).*
Lee et al. {Acta Crystallographica, Section E: Structure Reports Online (2009), 65(12), m1600 and Supporting Information on pp. sup-1 to sup-4 (Year: 2009).*
Dillinger et al. {Dalton Transactions, 2007, pp. 3562-3571 (Year: 2007).*
Alessandro Prudente et al., "Nitric oxide coating polypropylene mesh increases angiogenesis and reduces inflammatory response and apoptosis," International Urology and Nephrology, 2017, pp. 597-605.
Benedetta Bussolati et al., "Vascular endothelial growth factor receptor-1 modulates vascular endothelial growth factor-mediated angiogenesis via nitric oxide," American Journal of Pathology, vol. 159, No. 3, Sep. 2001.
Chih-Chin Tsou et al, "Iron(III) Bound by Hydrosulfide Anion Ligands: NO-Promoted Stabilization of the [FeIII-SH] Motif", Journal of the American Chemical Society (JACS), 2014, 136, pp. 9424-9433.
Shou-Cheng Wu et al, "Water-Soluble Dinitrosyl Iron Complex (DNIC): a Nitric Oxide Vehicle Triggering Cancer Cell Death via Apoptosis", Inorganic Chemistry, 2016, 55, pp. 9383-9392.

* cited by examiner

*Primary Examiner* — Laura L Stockton
(74) *Attorney, Agent, or Firm* — CKC & Partners Co., Ltd.

(57) ABSTRACT

The present disclosure provides a compound for releasing nitric oxide; the compound has the structure of formula (I):

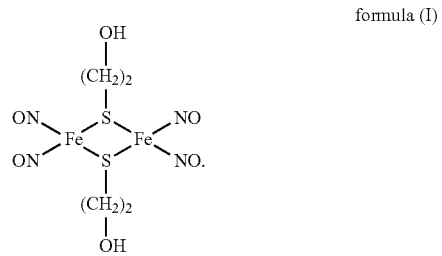

formula (I)

The present disclosure also provides a pharmaceutical composition containing the compound of formula (I). The present disclosure further provides a method of releasing nitric oxide, the method includes: administrating the compound of formula (I). The present disclosure also provides a method of treating disease in a patient, the method includes administrating a therapeutically effective amount of the compound of formula (I). The present disclosure also provides the method for synthesizing the compound of formula (I).

6 Claims, 25 Drawing Sheets

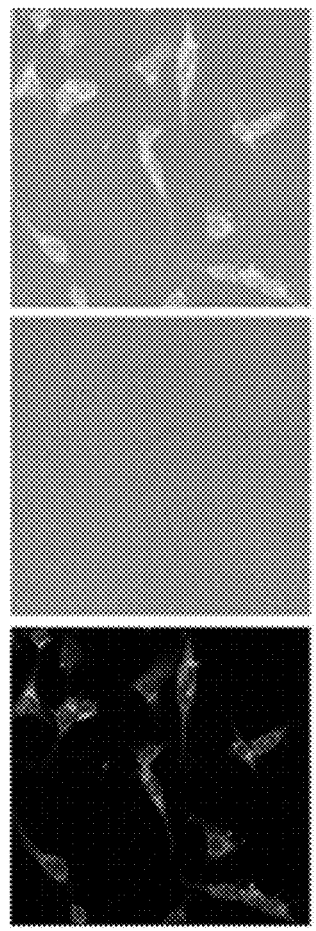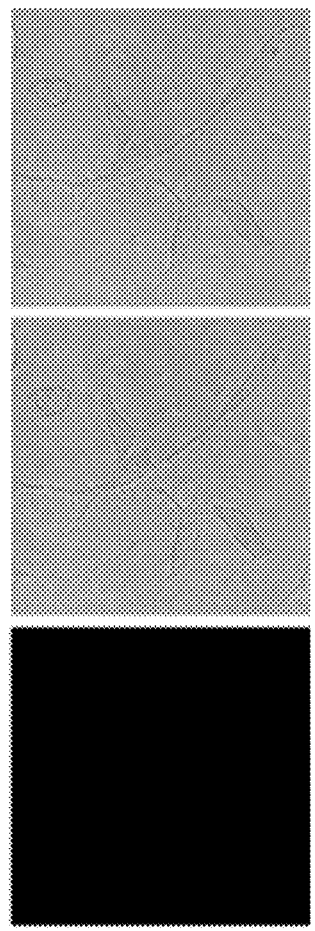

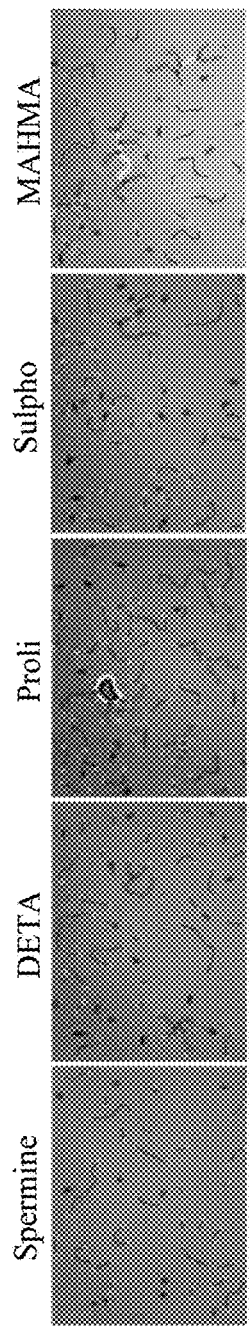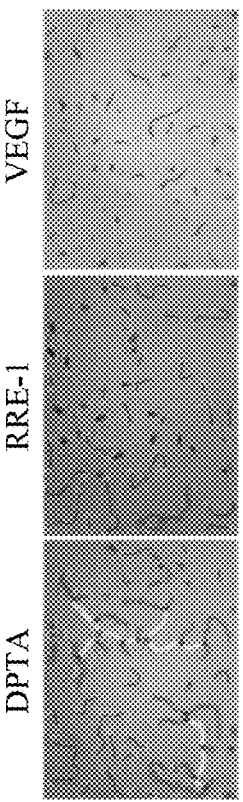
Fig. 5A Spermine
Fig. 5B DETA
Fig. 5C Proli
Fig. 5D Sulpho
Fig. 5E MAHMA
Fig. 5F DPTA
Fig. 5G RRE-1
Fig. 5H VEGF

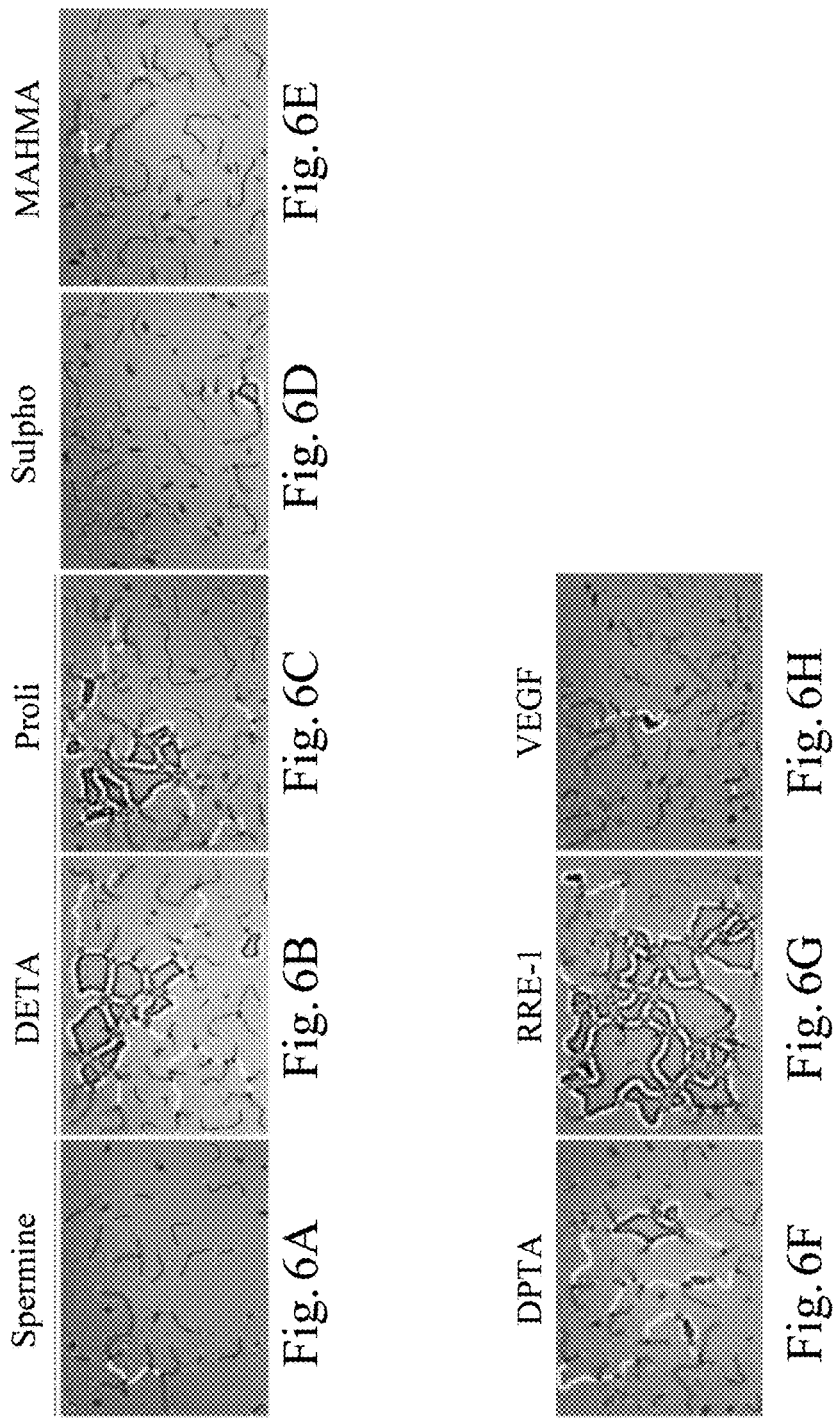

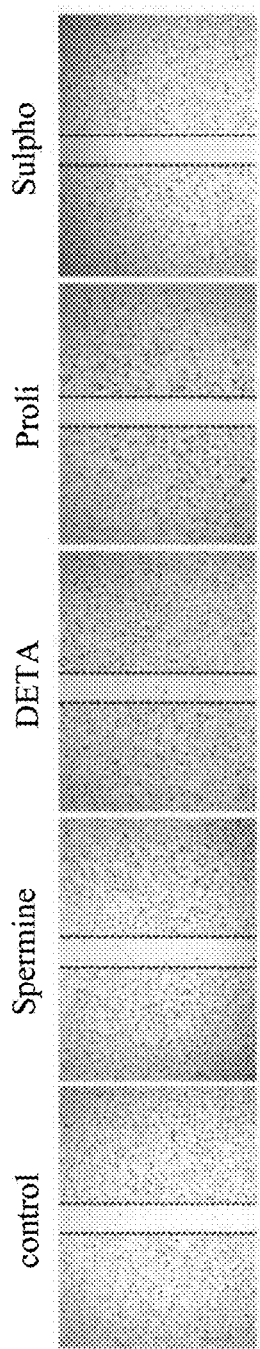
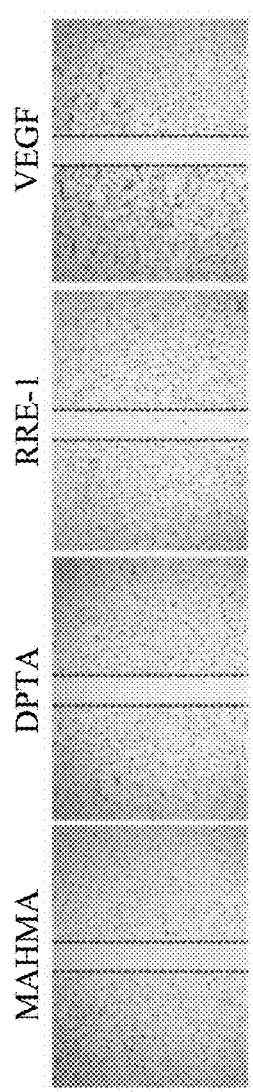
Fig. 8A control  Fig. 8B Spermine  Fig. 8C DETA  Fig. 8D Proli  Fig. 8E Sulpho
Fig. 8F MAHMA  Fig. 8G DPTA  Fig. 8H RRE-1  Fig. 8I VEGF

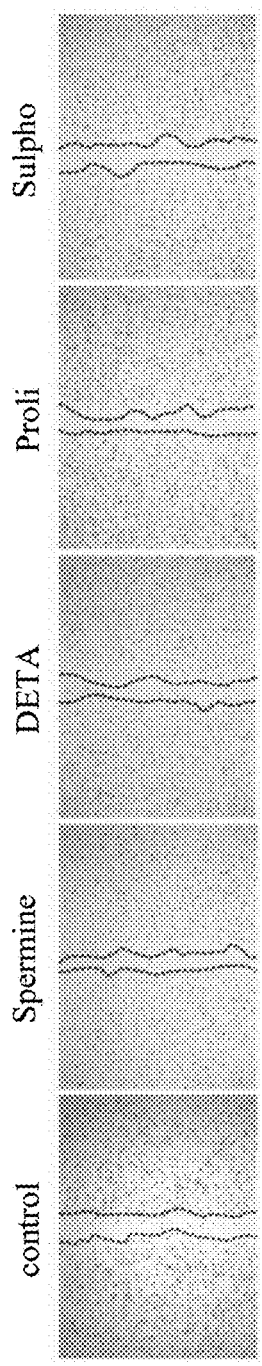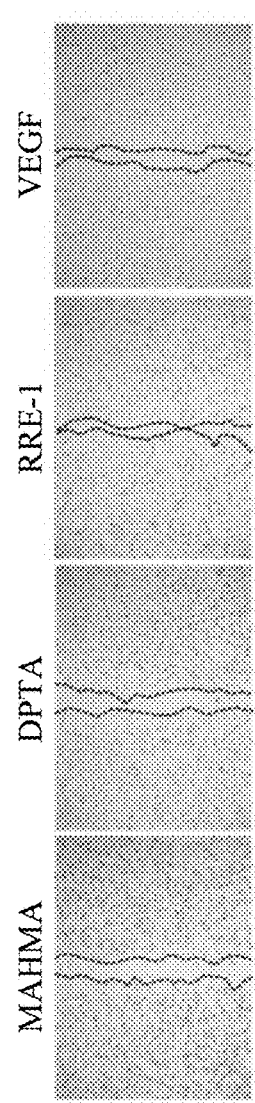

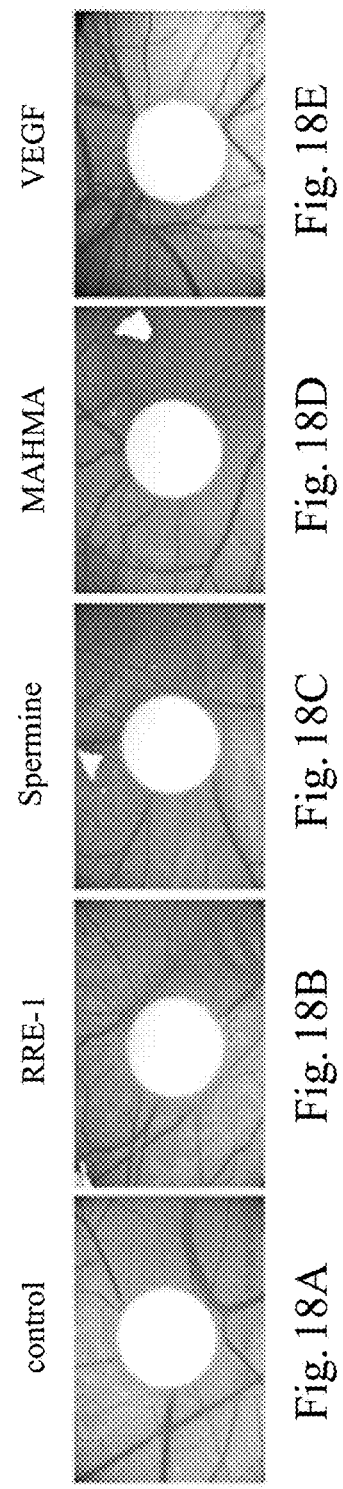

control   RRE-1    Spermine  MAHMA    VEGF

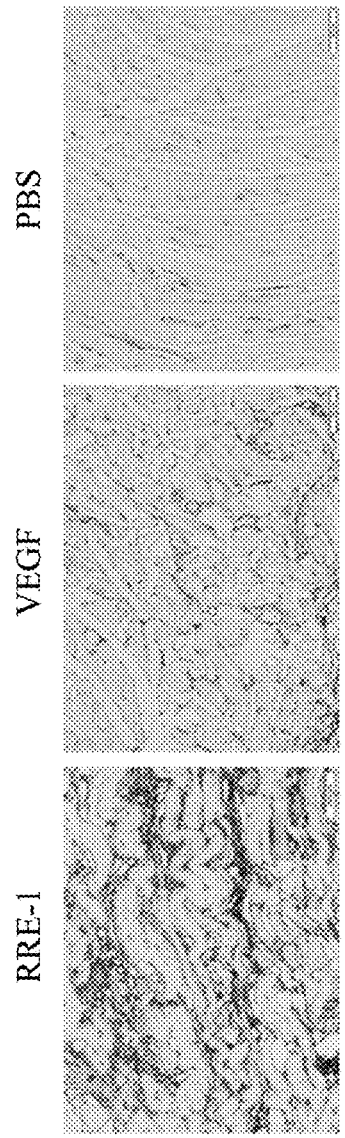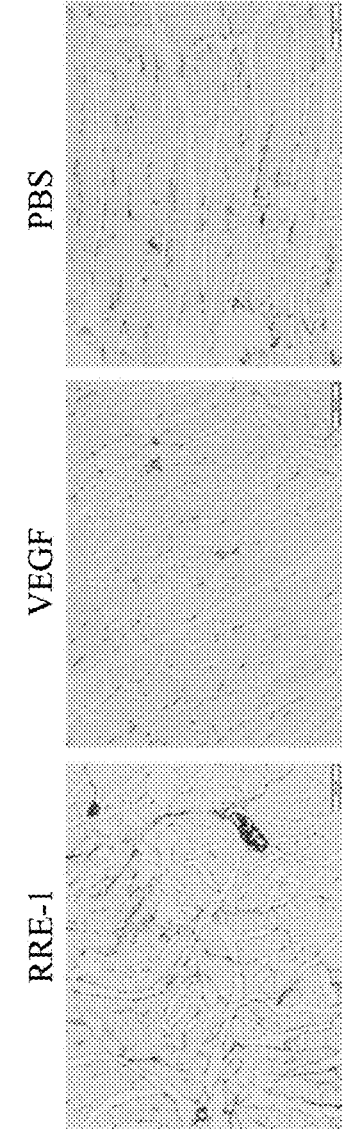

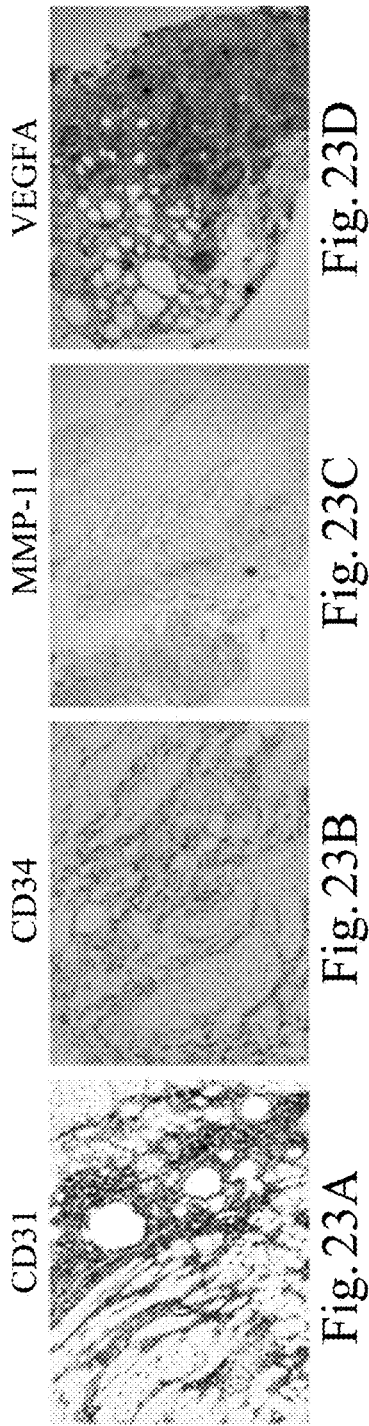
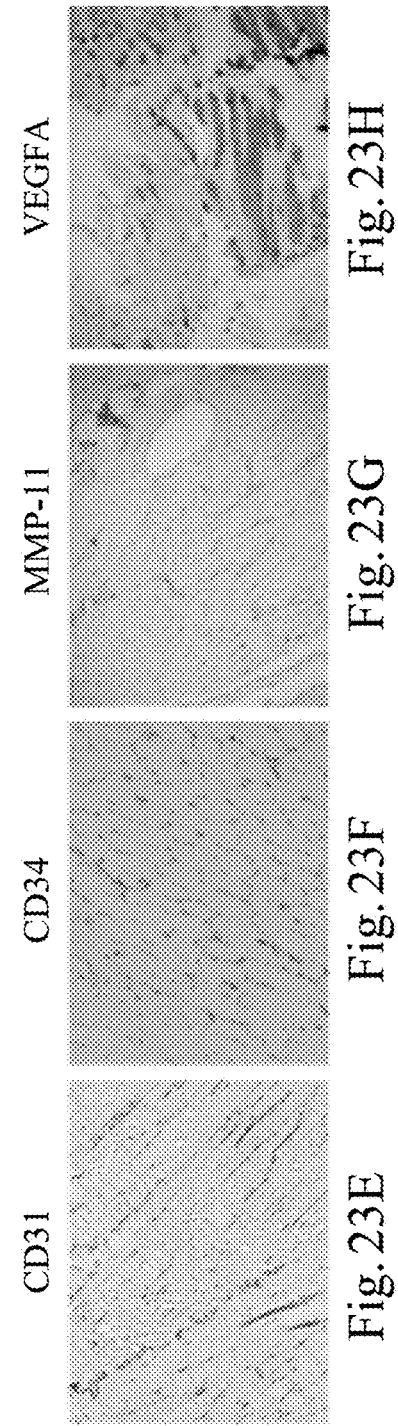

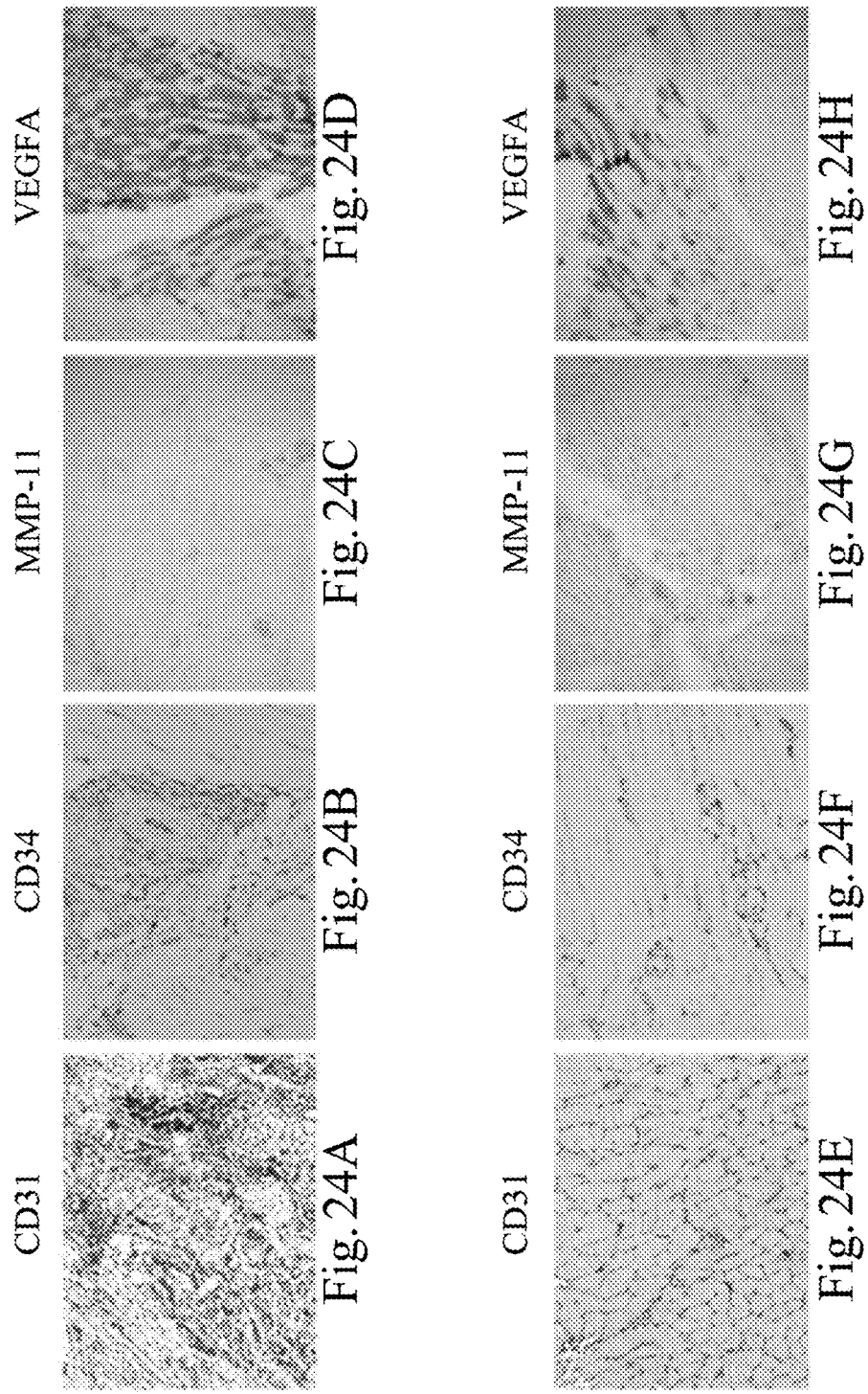

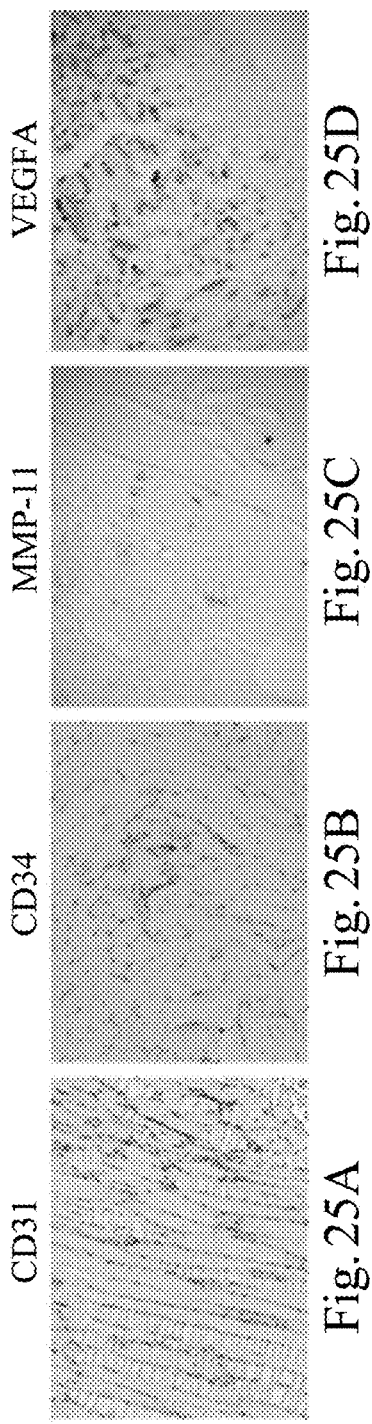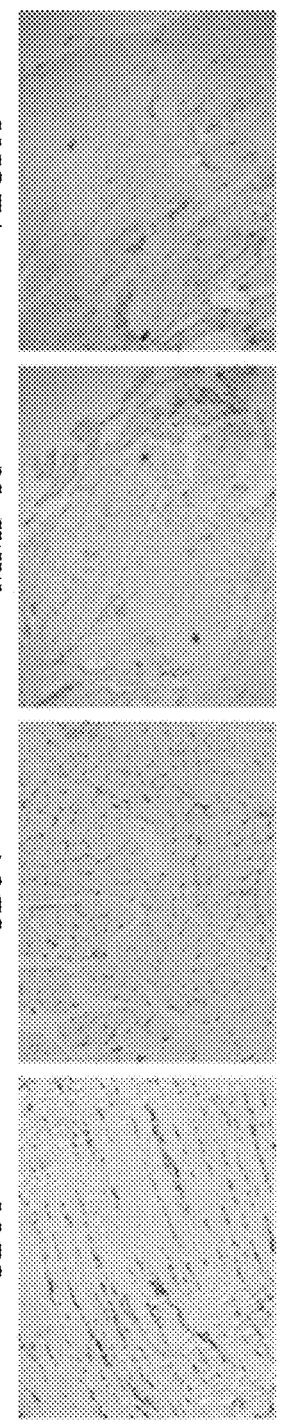
Fig. 25A  Fig. 25B  Fig. 25C  Fig. 25D
Fig. 25E  Fig. 25F  Fig. 25G  Fig. 25H

NITRIC OXIDE RELEASING COMPOUND, PHARMACEUTICAL COMPOSITION, USE AND SYNTHESIS METHOD THEREOF

CROSS-REFERENCE TO RELATED APPLICATION

This application claims priority to Taiwan Application Serial Number 106136571, filed Oct. 24, 2017, which is herein incorporated by reference.

BACKGROUND

Field of Invention

The present invention relates to a nitric oxide releasing agent.

Description of Related Art

Nitric oxide (NO) is an important signaling molecule and an effector molecule in organisms. Nitric oxide relates to many physiological and pathological processes and has a wide range of physiological functions, such as vasodilatation, regulation of immune responses, neurotransmission, cell death, angiogenesis, promotion of endothelial cell growth, and wound healing.

Different concentrations of nitric oxide on physiological processes have very different regulatory mechanisms; for example, low concentrations of nitric oxide can promote cell growth, while high concentrations of nitric oxide can cause cell death. Since nitric oxide is a short half-life free radical, nitric oxide needs to exist within the target site with sufficient amounts to achieve the therapeutic effect. However, side effects may occur if excessive nitric oxide administrated to the recipient.

Because nitric oxide is unstable, it is very difficult to apply nitric oxide directly to biological individuals. Nitric oxide releasing agents, or nitric oxide donors, is a kind of compounds that release nitric oxide through enzymatic or non-enzymatic action in organisms and can store and provide nitric oxide. Nitric oxide releasing compounds can eliminate the shortcomings of nitric oxide itself, such as difficult to carry, difficult to quantify, and short half-life, so these compounds have a wide range of applications.

At present, some nitric oxide releasing agents have been developed for promoting angiogenesis and wound healing, such as Spermine (SP); diethylenetriamine (also called DETA), 1-(hydroxy-NNO-azoxy)-L-proline, disodium salt (also called Proli NONOate, or Proli); disodium (E)-1-sulfonatodiazen-1-ium-1,2-diolate (also called Sulpho NONOate, or Sulpho); (Z)-1-[N-Methyl-N-[6-(N-methyl-ammoniohexyl)amino]]diazen-1-ium-1,2-diolate (also called MAHMA NONOate, or MAHMA); and (Z)-1-[N-(3-aminopropyl)-N-(3-ammoniopropyl)amino]diazen-1-ium-1,2-diolate (also called DPTA NONOate, or DPTA). These compounds form and release nitric oxide mainly through electron transfer. These compounds have varying degrees of half-life in vivo, and the efficiency of releasing nitric oxide changes with the environmental variation of the action site.

In addition, the known types of nitric oxide releasing compounds may roughly be classified into four classes: diazenium, nitrosothiols, nitrobenzene derivatives, and metal nitrosyl complexes. Among the different classes of compounds, the nature of diazenium donors is unstable. Before reaching the target site, diazenium donors maybe decompose and release large amounts of nitric oxide during circulation of blood. The stability of nitrosothiols donors is also poor. Donors of nitrobenzene derivatives are thermodynamically stable under physiological conditions and release nitric oxide under photo-excitation, but they require high-energy UV excitation to release nitric oxide. Metal nitrosyl complexes, such as Russin's salt and sodium nitroprusside, have the property of releasing nitric oxide by light emission, but their stability is poor. Metal nitrosyl complexes are easily hydrolyzed in physiological conditions, and such donors are also metabolized rapidly into toxic cyanide in vivo; hence, the use scope of the complexes is limited.

SUMMARY

In some embodiments, the present disclosure provides a nitric oxide releasing compound having the structure of formula (I):

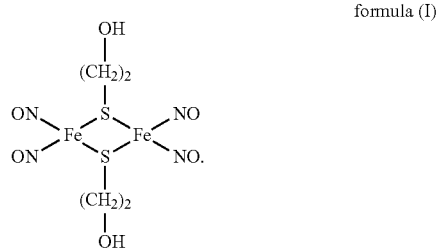

formula (I)

In some embodiments, the present disclosure provides a pharmaceutical composition comprising the compound of Formula (I) and a carrying agent.

In some embodiments, the present disclosure provides a method of releasing nitric oxide. The method includes: administrating the compound of formula (I) to a recipient.

In some embodiments, the present disclosure provides a method of treating disease in a patient. The method includes: administrating a therapeutically effective amount of a compound according to claim 1 to the patient, and releasing nitric oxide in the recipient.

In some embodiments, the present disclosure provides a method of synthesizing the compound of formula (I). The method includes: reacting iron pentacarbonyl ($Fe(CO)_5$) with sodium nitrite ($NaNO_2$) and 18-crown-6-ether to form $[Fe(CO)_3(NO)]^-$; and reacting $[Fe(CO)_3(NO)]^-$ with nitrosyl tetrafluoroborate ($NOBF_4$) to form an intermediate, followed by reacting the intermediate with 2-mercaptoethanol to obtain the compound of formula (I).

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows:

FIGS. 3A to 3F are microscopic images of cells according to an experimental example. FIGS. 3A to 3C are images of cells addicted RRE-1, and FIGS. 3D to 3F are control group images of cells addicted no RRE-1. FIGS. 3A and 3D are fluorescent images; FIGS. 3B and 3E are bright field images. FIG. 3C is a merged image of FIGS. 3A and 3B. FIG. 3F is a merged image of FIGS. 3D and 3E.

FIGS. 5A to 5H are respective images taken within 1 hour after addition of different nitric oxide releasing agents to cells according to an experimental example.

FIGS. 6A to 6H respectively show the images of cells in FIGS. 5A to 5H, the images were taken at the 24th hours after the respective various nitric oxide releasing agents were added to the cells.

FIGS. 8A to 8I are images of cells of in vitro wound healing test; the images were taken within 1 hour after the respective various nitric oxide releasing agents were added to the cells according to an experimental example.

FIGS. 9A to 9I are images of cells in FIGS. 8A to 8I, respectively. The images were taken at the 24th hours after the respective various of the nitric oxide releasing agents were added to the cells.

FIGS. 18A to 18E are images showing the angiogenesis of chicken embryos treated with the respective various nitric oxide releasing agents according to an experimental example.

FIGS. 22A to 22F are images of tissue slices stained with anti-eNOS antibody according to an experimental example, in which the tissues of FIGS. 22A to 22C are from the ischemic hindlimbs, and the tissues of FIGS. 22D to 22F are from the non-ischemic hindlimbs.

FIGS. 23A to 23H are tissue images according to an experimental example. The diabetic mice with ischemic hindlimbs were administrated with RRE-1, and then the tissue slices were stained with anti-CD31 antibody, anti-CD34 antibody, anti-MMP-11 antibody, and anti-VEGFA antibody, respectively. The tissue slices in FIGS. 23A to 23D were from the ischemic limbs and the tissue slices in FIGS. 23E to 23H were from non-ischemic limbs.

FIGS. 24A to 24H are tissue images according to an experimental example. The diabetic mice with ischemic hindlimbs were administrated with VEGF, and then the tissue slices were stained with anti-CD31 antibody, anti-CD34 antibody, anti-MMP-11 antibody, and anti-VEGFA antibody, respectively. The tissue slices in FIGS. 24A to 24D were from ischemic limbs, and the tissue slides in FIGS. 24E to 24H were from non-ischemic limbs.

FIGS. 25A to 25H are images according to an experimental example. The images showing ischemic diabetic mice were administrated with phosphate buffered saline (PBS), and then the tissue slides were respectively stained with anti-CD31 antibody, anti-CD34 antibody, anti-MMP-11 antibody, and anti-VEGFA antibody. The tissue slices in FIGS. 25A to 25D were from ischemic hindlimbs, and tissue slices from FIGS. 25E to 25H were from non-ischemic hindlimbs.

DETAILED DESCRIPTION

Figure 1:
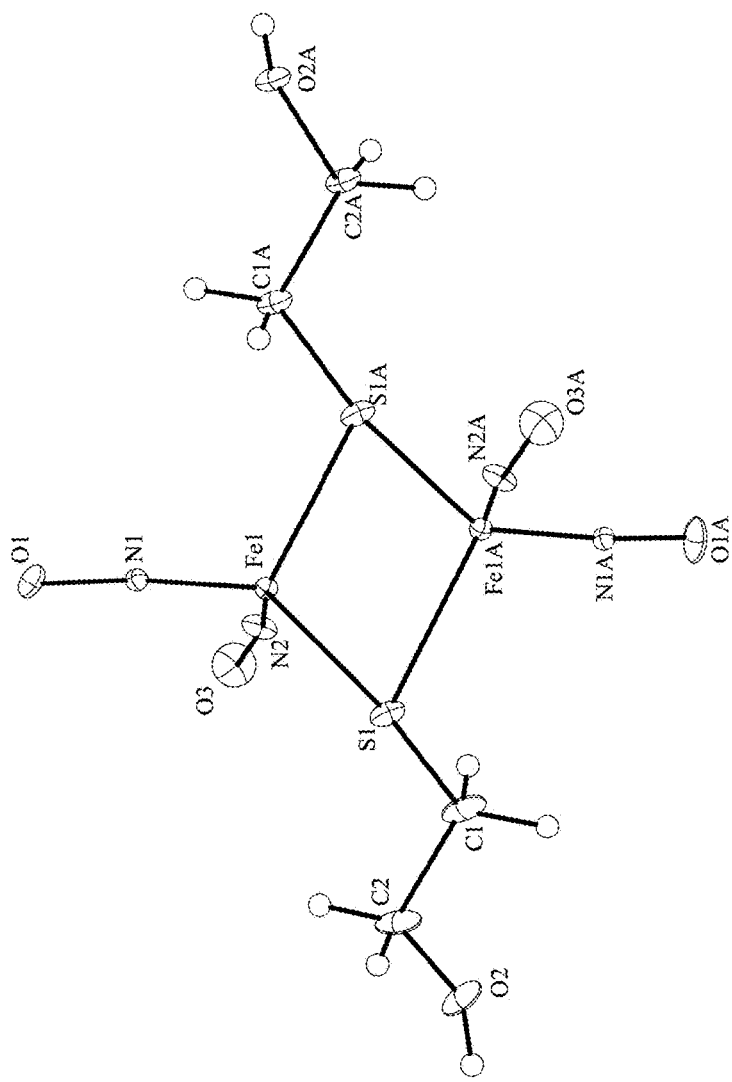
FIG. 1 shows the 3-dimensional molecular structure of the compound of the present disclosure through X-ray single crystal diffraction method.

Reference will now be made in detail to the present embodiments of the invention, examples of which are illustrated in the accompanying drawings. Wherever possible, the same reference numbers are used in the drawings and the description to refer to the same or like parts.

In this context and in the drawings, RRE-1 represents the compound of formula (I):

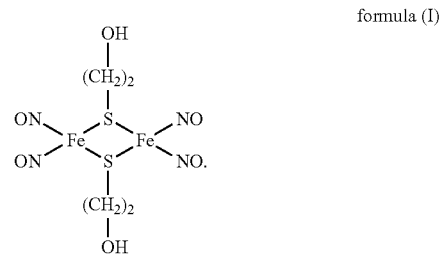

formula (I)

In at least one embodiment, a compound for releasing nitric oxide is provided, and the compound has the structure of formula (I). In an embodiment, the compound of formula (I) is soluble in water or an aqueous solution, and the compound releases nitric oxide in solution.

In at least one embodiment, there is provided a pharmaceutical composition comprising RRE-1 as an active ingredient, and further comprising a pharmaceutically acceptable carrying agent. The carrying agent adapts to various forms according to the formulation of different administration ways.

In at least one embodiment, the formulation of the pharmaceutical composition is in the form of injection, oral dosage, external ointment, dermal patch, or a wound dressing.

In at least one embodiment, the pharmaceutical composition is an injection formulation, in which the carrying agent is water or an aqueous solution, such as, normal saline or phosphate buffered aqueous solution (PBS). By intravenous injection, the pharmaceutical composition containing RRE-1 is administered into the body of the recipient.

In at least one embodiment, the pharmaceutical composition containing RRE-1 is applicable to humans or animals, such as domestic animals, poultry or pets. In some embodiments, animals are vertebrates, such as fish, reptiles, amphibians, birds or mammals.

In at least one embodiment, since RRE-1 is a nitric oxide releasing agent, a pharmaceutical composition containing RRE-1 is for promoting the in vivo physiological functions relating to nitric oxide in recipients, for example, to promote angiogenesis, vasodilation, or endothelial cell proliferation in recipients.

In at least one embodiment, since RRE-1 is a nitric oxide releasing agent, a drug containing RRE-1 can be prepared for treatment of diseases treated with nitric oxide releasing agents, e.g. treatment of diabetes, wounds, terminal circulation dysfunction, myocardial infarction, or stroke.

Preparation of RRE-1.

In at least one embodiment, RRE-1 can be synthesized through the following process:

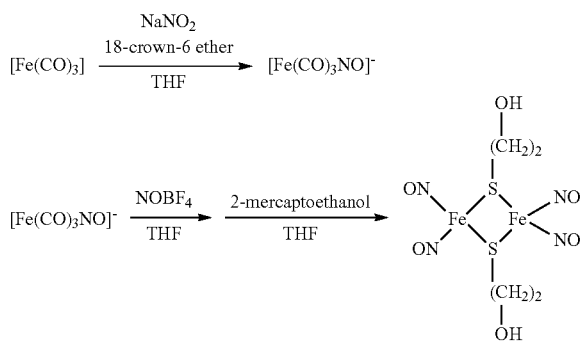

The preparation of RRE-1 contains two main processes:
(a) Reacting iron pentacarbonyl (Fe(CO) 5) with sodium nitrite (NaNO2) and 18-crown-6-ether to form [Fe(CO)3(NO)]⁻.
(b) Reacting [Fe(CO)₃(NO)]⁻ with nitrite tetrafluoroborate (NOBF₄) to form an intermediate, followed by reacting the intermediate with 2-mercaptoethanol to form RRE-1.

The preparation steps of RRE-1 are described in detail as follows:

Step 1: $NaNO_2$ (0.311 g, 4.5 mmol) and 18-crown-6-ether (1.189 g, 4.5 mmol) were weighed out and placed in a Schlenk tube, tetrahydrofuran (THF) (15 mL) was added, the mixture was stirred for one minute, then cooled in ice bath and kept stirring. A plastic syringe was used to extract $Fe(CO)_5$ (0.26 mL) into the Schlenk tube. The color of the supernatant changed from transparent to dark yellow, because [Fe(CO)₃(NO)]⁻ formed. The [Fe(CO)₃(NO)]⁻ compound was measured and its infrared (IR) spectral absorbance was 1978 s, 1875 vs, 1650 s cm-1 (THF).

Step 2: Then nitrite tetrafluoroborate (NOBF₄) (0.526 g, 4.5 mmol) was added, and the mixture was stirred continuously and rapidly under ice bath until no gas was produced. The red solution in Schlenk tube was drawn to another Schlenk tube immersed in liquid nitrogen, and infrared absorption of the red solution was 2088 s, 2038 vs 1806 s, 1760 vs cm-1 (THF).

Step 3: 2-mercaptoethanol (0.32 mL) was drawn into a plastic syringe, then injected into the Schlenk tube. Then an oil tube was connected to the Schlenk tube, and the mixture was stirred at room temperature. The solution turned from orange to reddish brown. After 6 hours reaction, there was no gas produced from the mixture. Then the IR absorption of the product was measured, which was 1749 s, 1774 s, 1809 vw cm-1 (THF).

Step 4: Then the Schlenk tube was dried and tetrahydrofuran (15 mL) was added to dissolve the product. Pure oxygen was added and the mixture was stirred for 5 minutes. The mixture was filtered to another degassed Schlenk tube and dried once more. The solid product was washed with hexane, and the supernatant was removed and dried to obtain red-brown RRE-1 solid.

Afterwards, the product was crystallized by double layer method in ether and hexane, and reddish brown lumps (0.193 g, 0.5 mmol) were formed after 5 days at −20° C., the yield was 50%. The product was then dissolved in the mixture of dimethyl sulfoxide (DMSO):PBS=1:99 for follow-up testing.

The structure of RRE-1 was analyzed by X-ray single crystal diffraction, the identification results were as follows: Fe1 . . . Fe1A 2.706 (1); Fe1-N(1) 1.672 (4); Fe—N 2.254 (1); Fe1-S1A 2.261 (1); N1-Fe—N2 117.95 (17); N1-Fe—S1 105.49 (13); N2-Fe—S1 110.51 N1-Fe1-Fe1A 120.72 (13); N2-Fe1-Fe1A 121.33 (13); S1-Fe1-Fe1A 53.31 (13) 4); S1A-Fe1-Fe1A 53.07 (4). Referring to FIG. 1, which is the 3-dimensional structure of RRE-1 reconstructed by X-ray single crystal diffraction method.

Figure 2:
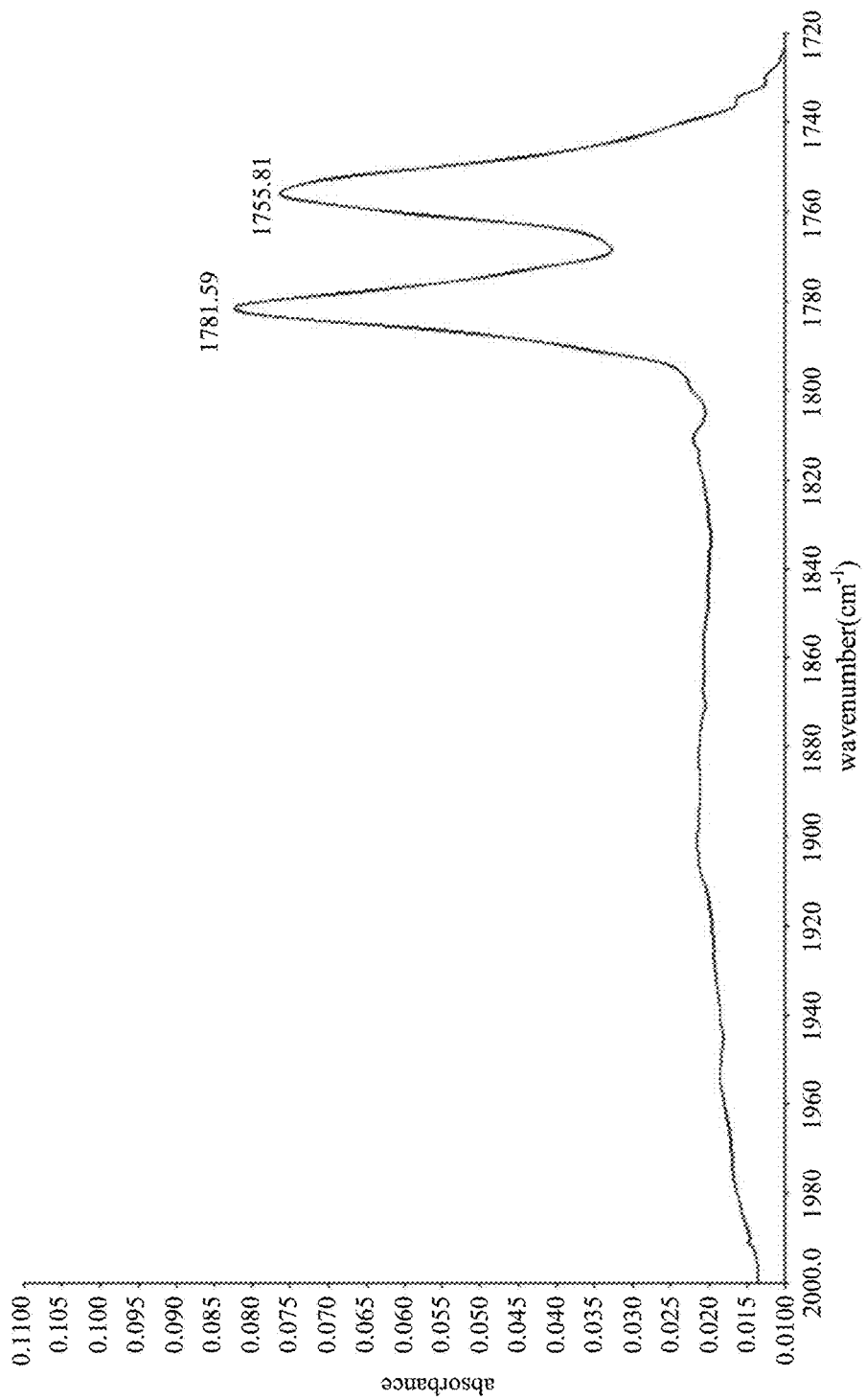
FIG. 2 shows an infrared absorption spectrum of the compound according to the present disclosure.

Referring to FIG. 2, which shows the infrared absorption spectrum of RRE-1 for identifying the characteristics of the functional groups. FIG. 2 shows two peaks of the IR absorption spectrum: 1781.59 and 1755.81. In addition, the absorbing characteristics of the infrared (IR) spectra of the aqueous phase as follows: IR $v_{N\ O}$: 1809 vw, 1774 s and 1749 s cm⁻¹ ($v_{N\ O}$) (THF); IR $v_{N\ O}$: 1814 vw, 1783 s, 1755 s cm⁻¹ ($D_2O$).

From the above experimental results, it was confirmed that the reaction product RRE-1 has the structure of formula (I).

Some experiments below show that RRE-1 can release nitric oxide in cells. The effects of RRE-1 and other known nitric oxide releasing agents on angiogenesis and wound healing were tested in vitro and in vivo animal experiments. Other various nitric oxide releasing agents tested were Spermine (SP), diethylenetriamine (DETA), 1-(hydroxy-NNO-azoxy)-L-proline, disodium salt (also called Proli); disodium (E)-1-sulfonatodiazen-1-ium-1,2-diolate (also called Sulpho); (Z)-1-[N-Methyl-N-[6-(N-methylammoniohexyl)amino]]diazen-1-ium-1,2-diolate (also called MAHMA); and (Z)-1-[N-(3-aminopropyl)-N-(3-ammoniopropyl)amino]diazen-1-ium-1,2-diolate (also called DPTA), and vascular endothelial growth factor (VEGF).

In the present disclosure, the cell line for the cell experiment is EAHY926 (human vascular endothelial cell line), and the mouse strain for the animal experiment is BALB/c Nude mouse.

Experimental Example 1: Nitric Oxide Releasing Ability of RRE-1

After EAHY926 cells were seeded on coverslips for 24 hours, RRE-1 at a concentration of 7.8 μM and a nitric oxide probe (FAOMe) were added. At the fourth hour after addition of RRE-1, the cells were washed three times with PBS, fixed with 4% formaldehyde for 30 minutes at room temperature. The coverslips were fixed with a mixture of PBS and glycerol (1:1) on glass slides, and the cells were observed with a confocal fluorescence microscope.

Please refer to FIGS. 3A to 3F, which are images of the cells labeled with a nitric oxide probe (FAOMe). FIGS. 3A to 3C are cells with the addition of RRE-1, and FIGS. 3D to 3F are control groups in which no RRE-1 was added to the cells. FIGS. 3A to 3C show that the cells in the group with the RRE-1 addition had the green fluorescent signal of fame. FIGS. 3D to 3F show that in the control group, there was no intracellular fluorescent signal. Therefore, RRE-1 is indeed a nitric oxide releasing agent which effectively releases nitric oxide in cells.

Experimental Example 2: Cell Viability Assay

In this experiment, 3-(4,5-cimethylthiazol-2-yl)-2,5-diphenyl tetrazolium bromide (also called MTT) was used for testing cell viability. MTT is a yellow compound and a dye that accepts hydrogen ions and acts on the respiratory chain of living cell mitochondria. Under the action of succinate dehydrogenase (SDH) and cytochrome C, the tetrazolium ring of MTT will be cracked to generate blue color crystals. The formation of crystals is proportional to the number of living cells (in dead cells, because there is no active succinate dehydrogenase, MTT cannot be reduced). The O.D value can indirectly represent cell viability because of the MTT reduction ability of living cells.

In the experiment, EAHY926 cells were respectively co-cultured with various concentrations of nitric oxide releasing agents: Spermine, DETA, Proli, Sulpho, MAHMA, DPTA, RRE-1 and VEGF at 37° C. for 24 hours, and the cell viability and the minimum doses were evaluated.

Figure 4:
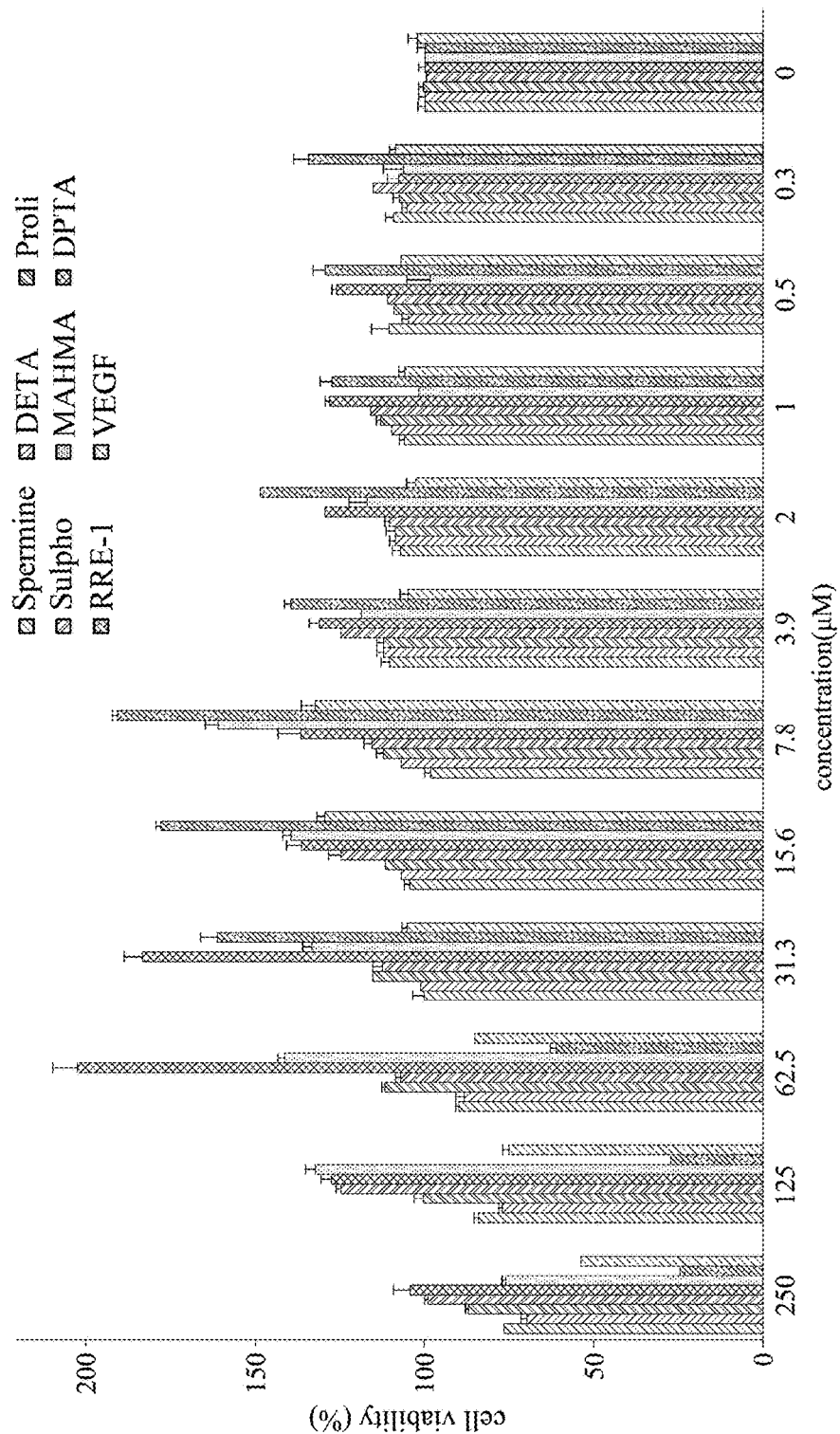
FIG. 4 is a bar chart of an experimental example, in which cell viability was tested with different nitric oxide releasing agents.

Please refer to FIG. 4, which shows that below the concentration of 15.6 µM, among the various nitric oxide releasing agents, RRE-1 promoted cell growth most significantly. In particular, at the concentration of 7.8 µM, RRE-1 worked best, followed by DPTA and MAHMA. In addition, the clinical medication VEGF does not work better than other commercially available nitric oxide-releasing agents on promotion of cell growth at various concentrations.

Experimental Example 3: Cell Development Index Assay

EAHY926 cells were seeded in cell culture plates at 37° C. When the amounts of cells reached to about 30% of the culture plates, the cultures were replaced with fresh medium and respectively added various nitric oxide releasing agents: Spermine, DETA, Proli, Sulpho, MAHMA, DPTA, RRE-1 and VEGF at the concentration of 7.8 µM. Microscopic images were taken within the first hour and the 24th hour after the addition of nitric oxide releasing agents, and the images were analyzed by "Angiogenesis Analyzer for ImageJ" software for analyzing cell development index. The analyzed cell development parameters include cell meshes, cell junctions and cell branches.

Please refer to FIGS. 5A to 5H and FIGS. 6A to 6H. In the analysis of cell development, the gray lines were represented as cell branches of the cell-cell junction, and the more lines mean more growth of the cells. In addition, when the cells were more developed because they had more cell branches, the cells were represented by white lines. As the degree of cell development increased, cell junctions (dark gray dots) became more. Further, the cells enclosed multiple circles (black lines) which were called cell meshes. FIGS. 6A to 6H show that the degree of cell development was highest in the RRE-1 (FIG. 6G) treatment group.

Figure 7A:
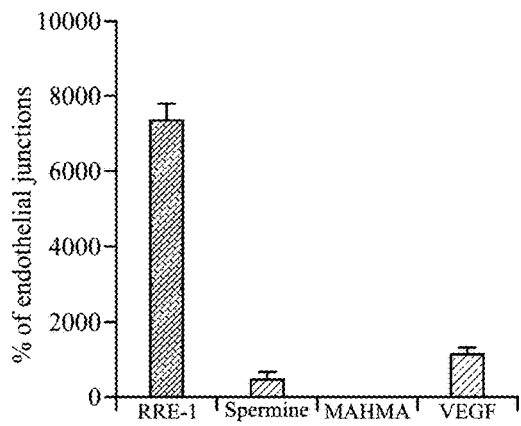
FIG. 7A is a bar chart showing the degree of cell development tested with the respective various nitric oxide releasing agents according to an experimental example.
Figure 7B:
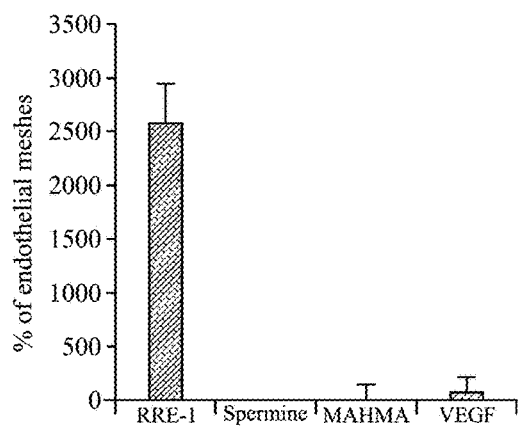
FIG. 7B is a bar chart showing the degree of cell development tested with the respective various nitric oxide releasing agents according to an experimental example.
Figure 7C:
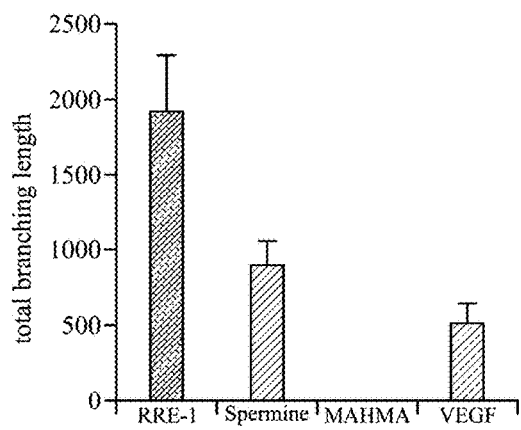
FIG. 7C is a bar chart showing the degree of cell development tested with the respective various nitric oxide releasing agents according to an experimental example.

Referring to FIGS. 7A to 7C, which show further quantification results of cell meshes, cell junctions and cell branches. The results indicate that regarding numbers of cell meshes, number of intercellular junction and number of branches, among the nitric oxide releasing agents, RRE-1 had the most significant effect. FIG. 7A shows that regarding the numbers of endothelial junctions, the effects of the groups were ranked as RRE-1>VEGF>Spermine>MAHA. FIG. 7B shows that regarding the numbers of endothelial meshes, the effects of the groups were ranked as RRE-1>VEGF>MAHMA>Spermine. FIG. 7C shows that regarding the total branching lengths, the effects of the groups were ranked as RRE-1>Spermine>VEGF>MAHMA.

From the above results, it is known the promotion effects of cell proliferation and growth of the various nitric oxide release agents are different, but in the cell proliferation and the cell development index, RRE-1 has the most significant effect.

Experimental Example 4: Wound Healing Assay

EAHY926 cells were seeded in cell culture plates at 37° C. When the amounts of the cells reached to about 80%, the cultures were replaced with fresh culture medium and were respectively added 7.8 µM concentration of the nitric oxide release agents: Spermine, DETA, Proli, Sulpho, MAHMA, DPTA, RRE-1 and VEGF. A 1 millimeter (mm) wide line was scraped off in a culture plate, and images of the culture were taken within the first hour and the 24th hour to record and quantify the percentage of wound healing.

Please refer to FIGS. 8A to 8I, which are images taken within the first hour after addition of the respective various nitric oxide release agents. Images from FIGS. 9A to 9I are cells of FIGS. 8A to 8I, respectively, which were taken at the 24th hour after addition of the respective various nitric oxide releasing agents to the cells. The images show that RRE-1, VEGF, Spermine, DPTA and Proli had more significant effects on wound healing.

Figure 10:
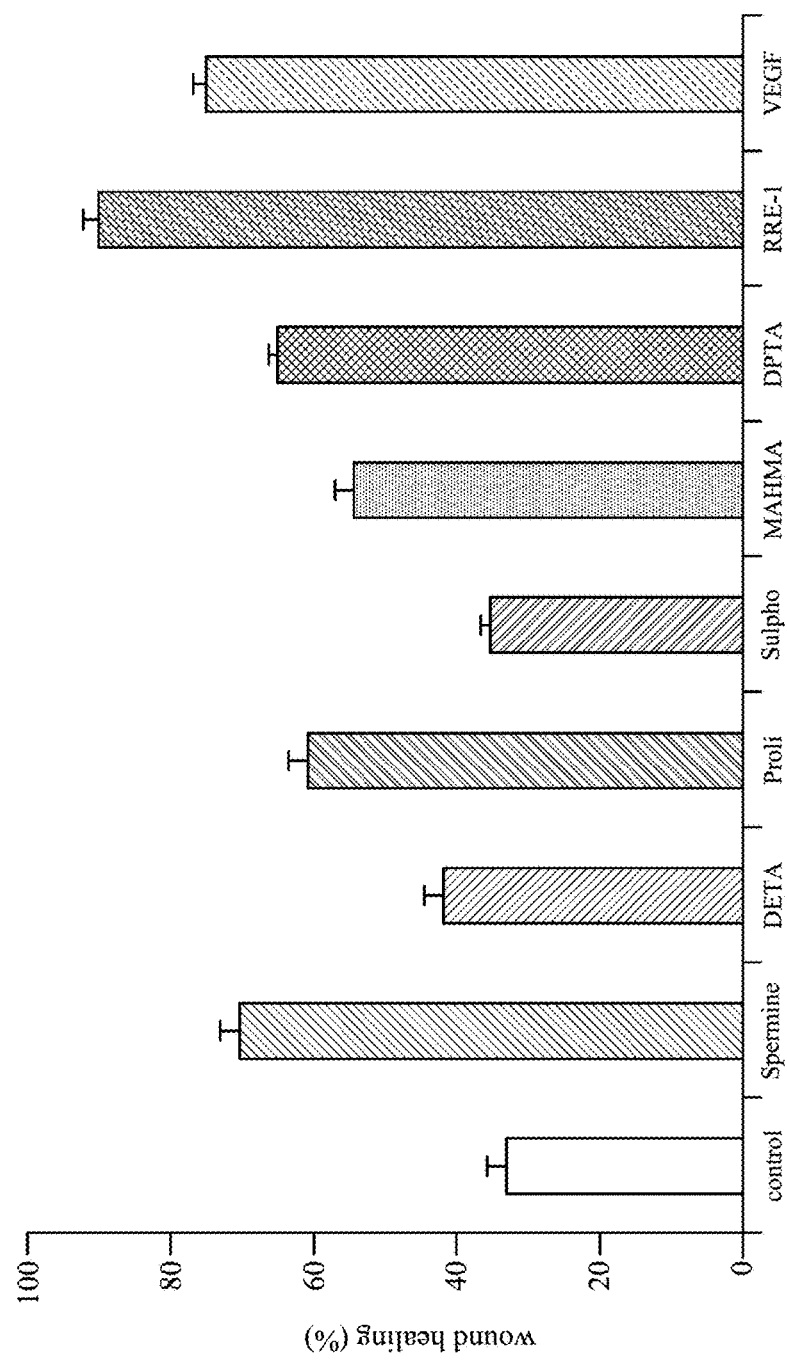
FIG. 10 is a bar chart quantified from the experiment of FIGS. 9A to 9I.

Please refer to FIG. 10, which is a quantitative result of the experiment of FIGS. 9A to 9I and shows that RRE-1 has the most significant effect on wound healing test.

Figure 11:
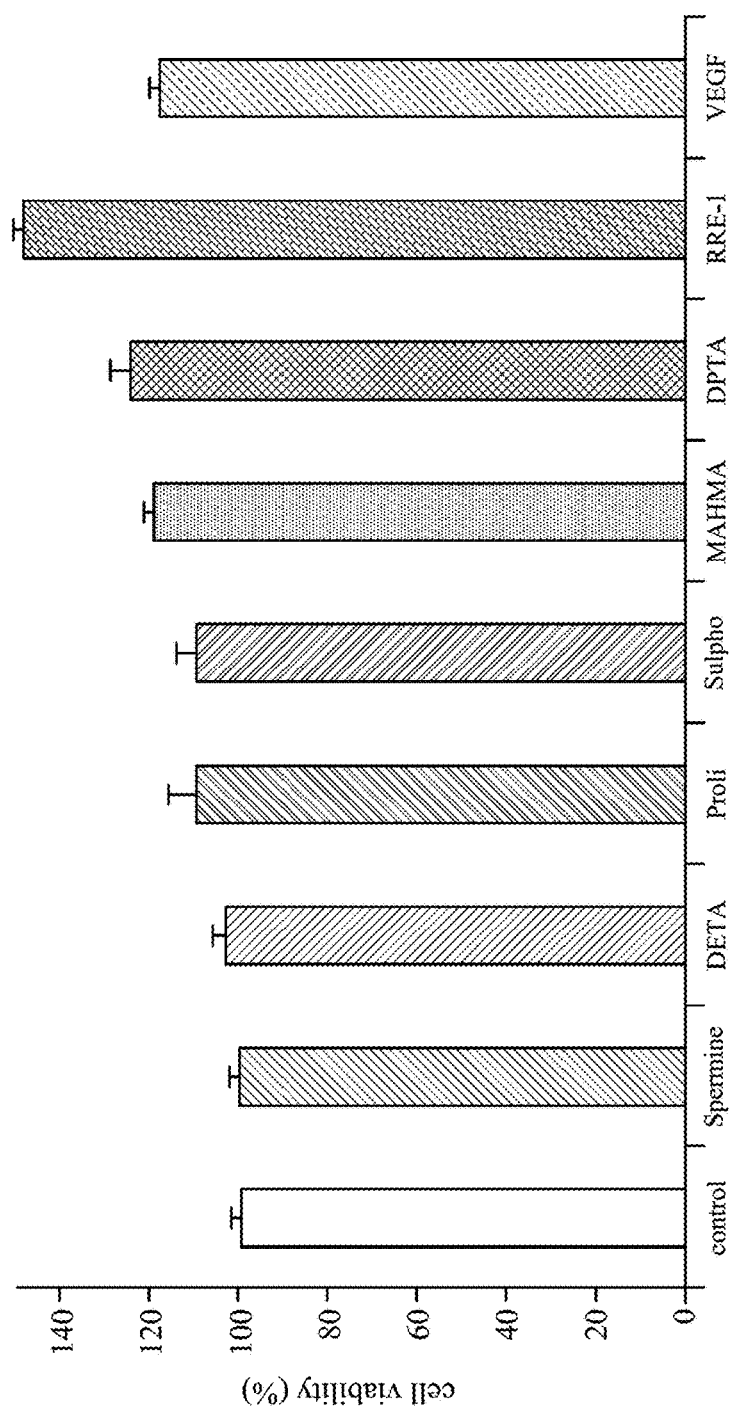
FIG. 11 is a bar chart showing the cell viability of the cells of FIGS. 9A to 9I according to an experimental example.

In the present experimental example, then the cell viability was assayed by adding MTT reagent to the various cell cultures of wound healing test. The results are shown in FIG. 11, among all of the groups, the group treated with RRE-1 had the highest cell viability. The result corresponds to the result of FIG. 4. In FIG. 11, the effects of cell viability were ranked as RRE-1>DPTA>MAHMA. The trend is similar to the result of FIG. 10.

Experimental Example 5: Western Blot Assay

In the literature, nitric oxide releasing agents have the potential for promoting angiogenesis and wound healing in vivo, and are also clinically useful agents that can effectively promote the expression of vascular endothelial growth factor receptor 2 (VEGFR2). Therefore, this experiment intended to test the effect of the respective various nitric oxide releasing agents on the expression of angiogenesis-related proteins (e.g., TIE-2, and VEGFR-2). Hence, different nitric oxide releasing agents were added to the cell cultures, respectively, and the expressions of the two proteins TIE-2 and VEGFR-2 were analyzed by Western blotting.

EAHY926 cells were seeded in cell culture dishes at 37° C. When the amounts of the cells reached to about 80% of culture plates, the cultures were replaced with new media with 7.8 µM of nitric oxide releasing agents (RRE-1, RRE-2, Spermine, MAHMA and VEGF) respectively. After 24 hours incubation, the cultures were washed with PBS three times and added 250 microliters (µL) of cell lysis buffer, then the cells were scraped and the proteins of the cells were extracted for Western blot experiment.

Figure 12:
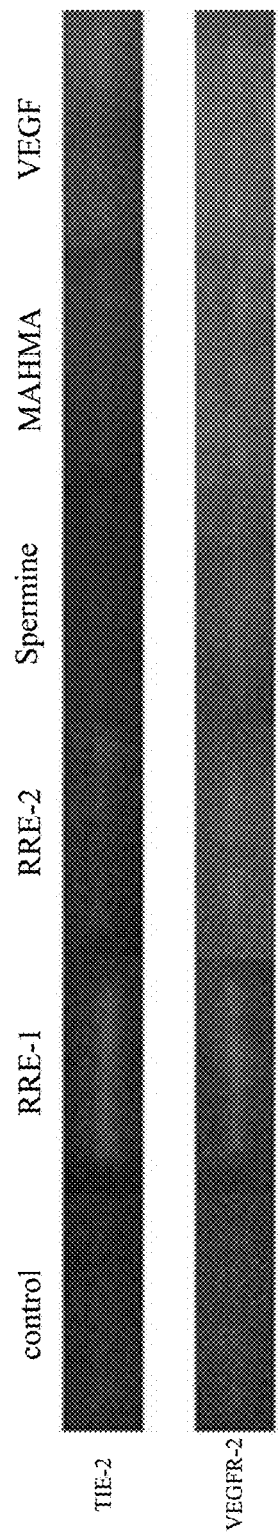
FIG. 12 shows a Western Blot image according to an experimental example.

Please refer to FIG. 12, which is western blot results of cells treated with various nitric oxide releasing agents. FIG. 12 shows that RRE-1 induced increased expression of proteins TIE-2 and VEGFR-2 most significantly after incubation of EAHY926 cells with 7.8 µM of nitric oxide releasing agents for 24 hours. The commercially available nitric oxide releasing agent, Spermine and MAHMA, and clinical medication VEGF, only induced a small amount of proteins TIE-2 and VEGFR-2 expression.

Experimental Example 6: In Vivo Angiogenesis Assay (DIVAA) in Mice

This experiment was carried out by a kit of in vivo angiogenesis assays to test the nitric oxide release agents: Spermine, DETA, Sulpho, MAHA, DPTA, RRE-1, and VEGF, wherein VEGF was as the positive control.

Immunodeficient nude mice (6 in each group) were fixed on the operating table and anesthetized (1-3% isoflurane/100% oxygen, flow rate 1 L/min). After the mice were fixed, two 1 cm incisions were respectfully cut on the left and right back of the mice with a surgical knife. Soft tubes containing mixtures of cell nutrient agents and 7.8 µM of respective nitric oxide releasing agents were prepared. These soft tubes were implanted into the back of the mice, then the wounds were washed with normal saline and were stitched. After 20 days, the soft tubes were removed and the hemoglobins within the soft tubes were released. The total amounts of hemoglobin were analyzed by ELISA analyzer for obtaining the correlation parameters of angiogenesis.

The respective various nitric oxide releasing agents tested in this experiment were Spermine, DATE, Prole, Sulpho, MAHMA, DPTA, RRE-1 and VEGF. The control group was the conditioned of the soft tube without nitric oxide releasing agents.

Figure 13:
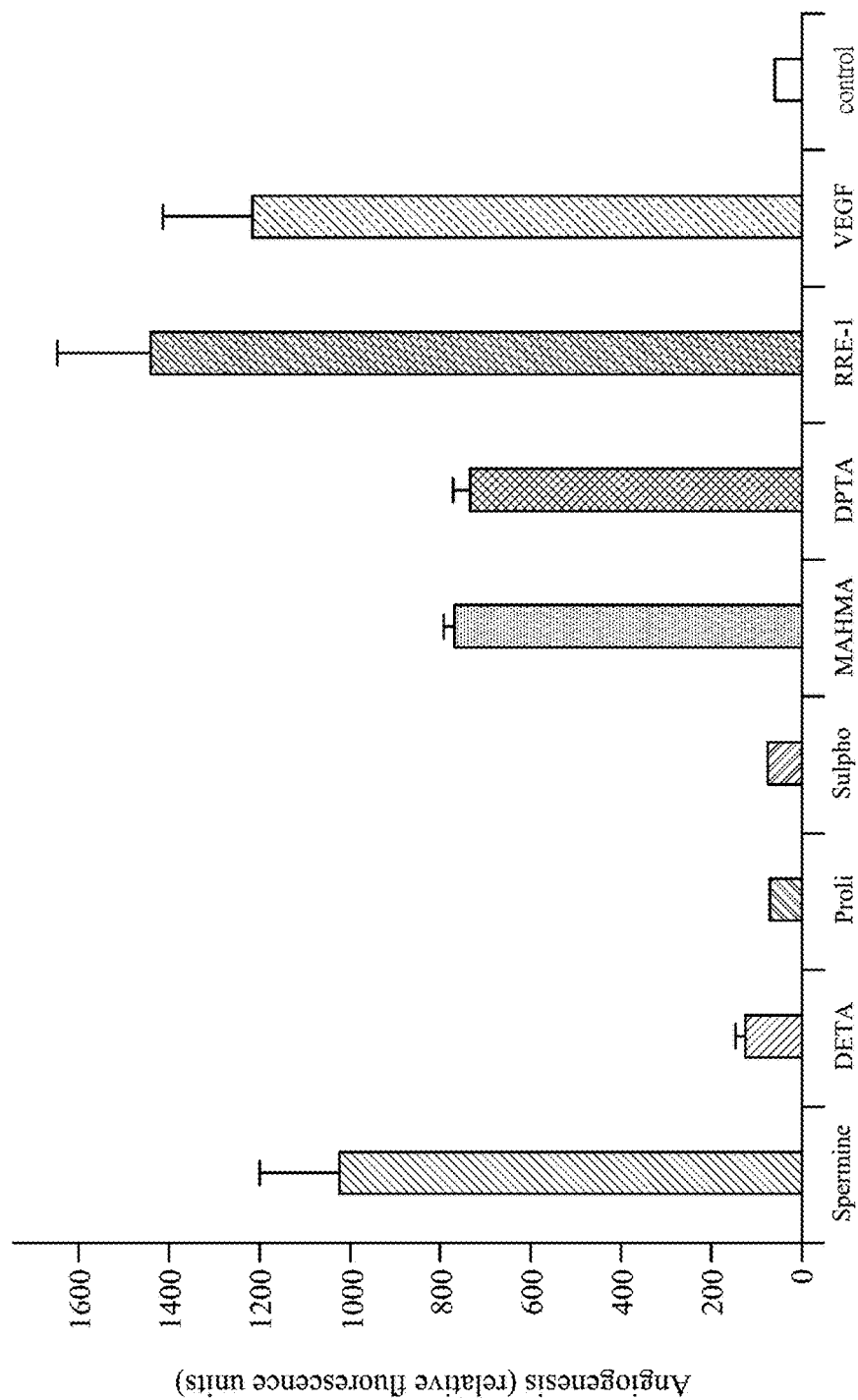
FIG. 13 is a bar chart showing the angiogenesis of mice treated with the respective various nitric oxide releasing agents according to an experimental example.
Figure 14:
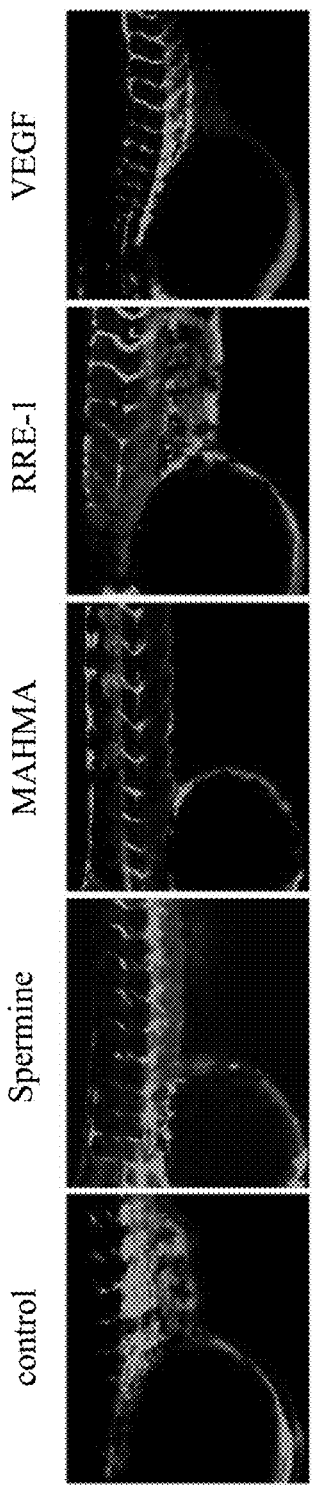
FIGS. 14A to 14E are images showing angiogenesis of zebrafish embryos according to an experimental example. The images were taken within one hour after the respective various nitric oxide releasing agents were added to the embryos.
Figure 15:
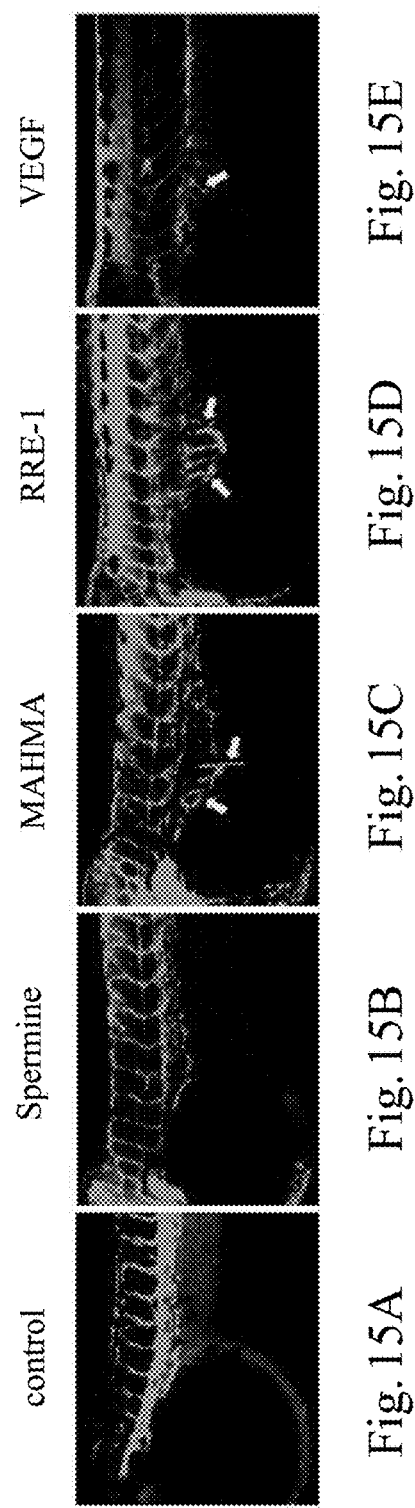
FIGS. 15A to 15E are images of the zebrafish embryos in FIGS. 14A to 14E, respectively. The images were taken within the 24th hour after addition of the respective various nitric oxide releasing agents.
Figure 16:
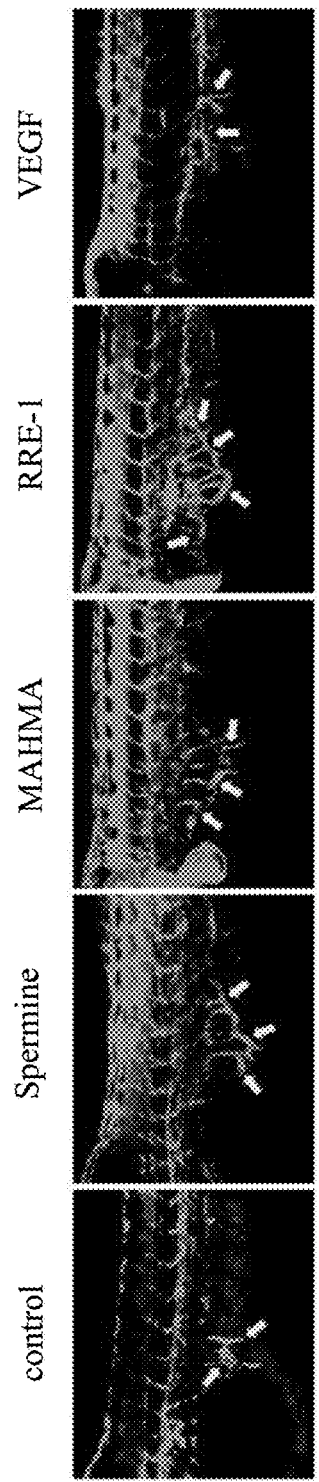
FIGS. 16A to 16E are images of the zebrafish embryos in FIGS. 14A to 14E, respectively. The images were taken within the 48th hour after addition of the respective various nitric oxide releasing agents.

FIG. 13 shows that after the soft tubes were implanted in the mice for twenty days, among the various nitric oxide releasing agents at concentration of 7.8 µM, RRE-1 can significantly promote angiogenesis inside the soft tubes, followed by VEGF and Spermine.

The above results show that RRE-1 either in vitro or in vivo has efficacies of cell proliferation and angiogenesis. The effect of RRE-1 is more significant than the effect of VEGF; therefore, RRE-1 can be a potential drug for clinical treatment relating to angiogenesis.

Experimental Example 7: In Vivo Angiogenesis Assay in Zebrafish

In this experiment, zebrafish with fluorescence gene Tg (fli1: EGFP) y1 were used for in vivo angiogenesis analysis. The zebrafish nutrient solutions were respectively added with the respective various nitric oxide releasing agents at 7.8 µM concentration. The zebrafish were incubated with nitric oxide releasing agents for 24 to 48 hours. The confocal microscopy images were taken at the beginning, the 24th hour, and the 48th hour after incubation, and semi-quantitative analysis of neovascularization in zebrafish oocysts was performed.

The nitric oxide releasing agents tested in this experiment were Spermine, MAHMA, RRE-1 and VEGF, and condition of the control group was the nutrient solution without nitric oxide releasing agent.

FIGS. 14A to 14E show images taken within the first hour after addition of the nitric oxide releasing agents. FIGS. 15A to 15E are images taken within the 24th hour after addition of the nitric oxide releasing agents. FIGS. 16A to 16E are images taken within the 48th hour after addition of nitric oxide releasing agents. Neovascularization in the zebrafish oocyst area is indicated by the white arrows.

Figure 17:
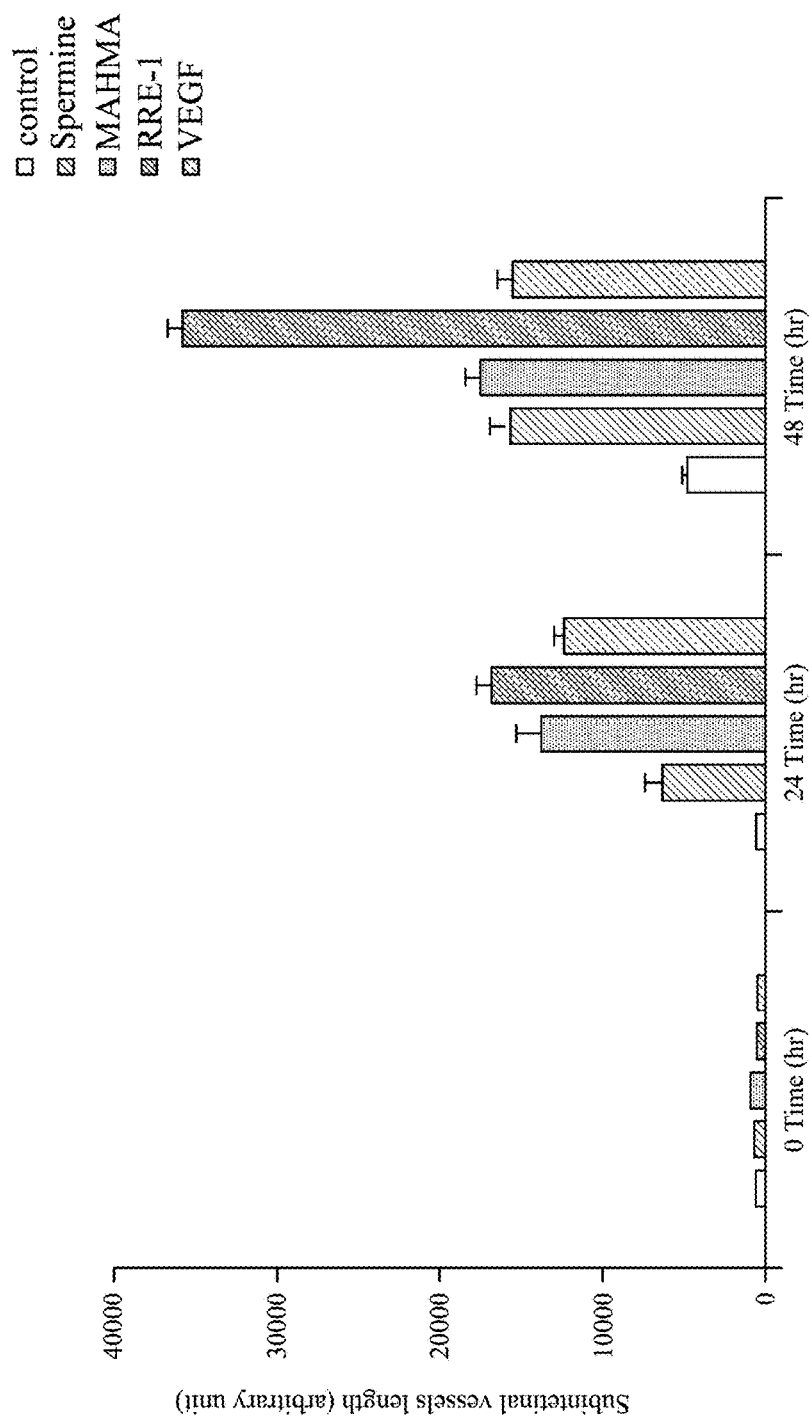
FIG. 17 is a bar chart quantified from the experiment of FIGS. 14A to 14E, FIGS. 15A to 15E and FIGS. 16A to 16E.
Figures 19A, 19B, 19C, 19D, 19E:
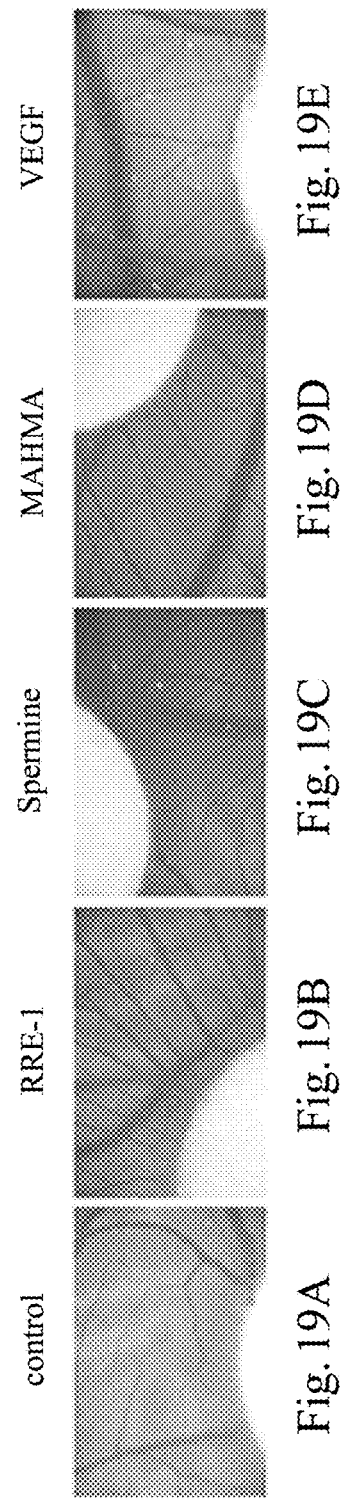
FIGS. 19A to 19E are partially enlarged images of FIGS. 18A to 18E, respectively.

FIG. 17 shows the quantitative results of the experiments of FIGS. 14A to 14E, FIGS. 15A to 15E, and FIGS. 16A to 16E. FIG. 17 shows that RRE-1 and MAHMA were the most effective nitric oxide releasing agents when the various nitric oxide releasing agents co-cultured with zebrafish at concentration of 7.8 µM for 24 hours. In the 48th hour after incubation, RRE-1 has the most significant effect on promoting angiogenesis, followed by MAHMA.

It is noted that in the above results, the clinical medication VEGF was not effective as expected, and its effect was even worse than the effects of other commercially available nitric oxide releasing agents. Therefore, the above results can verify that RRE-1 is very potent for angiogenesis.

Experimental Example 8: Chicken Chorioallantoic Membrane Assays (CAM)

In this experimental example, the insemination eggs were placed on the egg rack and the eggs' gas chamber were placed upwards in the hatching incubator. After incubation for 6 days, the eggs were screened with an egg detector, and the insemination eggs with hatching embryos were selected. Then, small holes were respectively drilled on the air chamber end (blunt end) and a side of the selected eggs, and 7.8 µM of the respective various nitric oxide releasing agents were injected through the small holes at the blunt end, sterilized filter films were covered on the hole of the air chamber, and then ventilation tapes were put on. The eggs were continuously incubated in the incubator. After 2 days of culture, the eggs were poked and placed in Petri dishes to observe and recorded by a camera.

The nitric oxide releasing agents tested in this experiment were RRE-1, Spermine, MAHMA and VEGF. The condition of the control group was the eggs with no addition of nitric oxide releasing agents.

Figure 20:
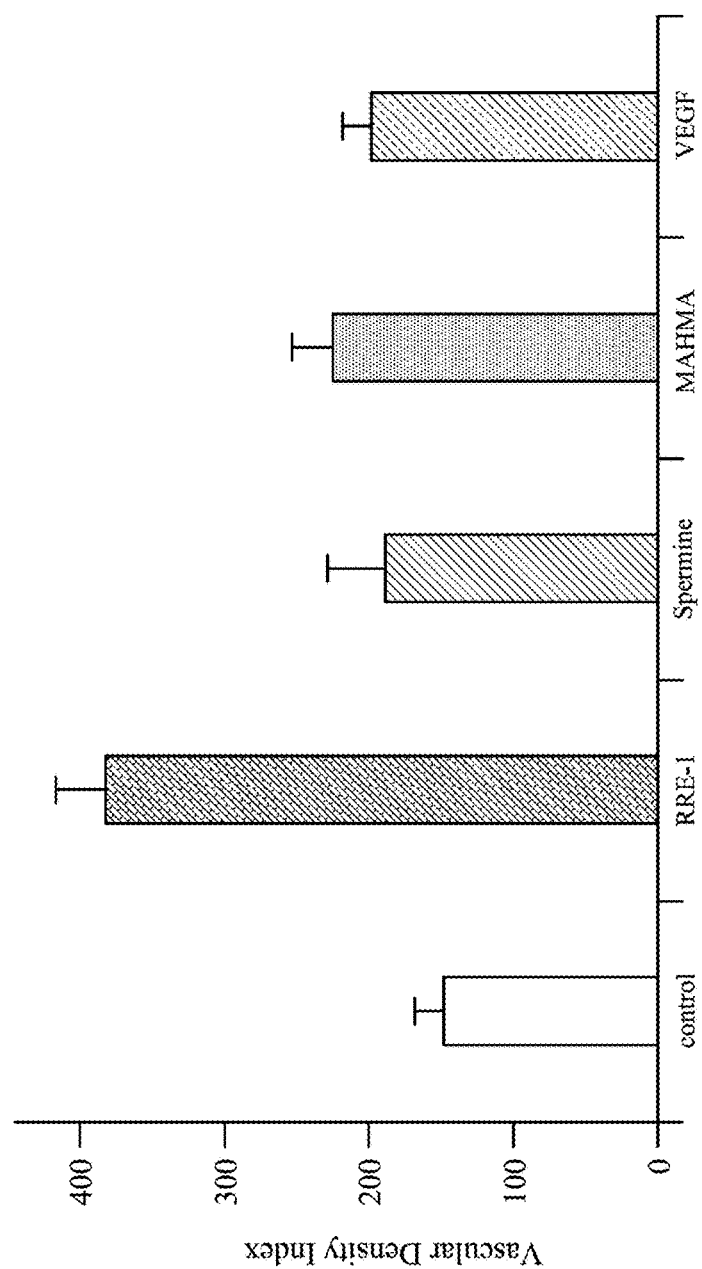
FIG. 20 is a bar graph quantified from the experiment of FIGS. 18A to 18E.

FIGS. 18A to 18E are images of chicken embryos, and FIGS. 19A to 19E are partially enlarged images of FIGS. 18A to 18E, respectively. FIG. 20 shows the quantitative results of the experiment of FIGS. 18A to 18E. FIG. 20 shows that among the nitric oxide releasing agents, RRE-1 has the most significant effect on angiogenesis, followed by MAHMA. The angiogenesis effect of clinical medication VEGF was similar to that of the commercially available nitric oxide releasing agent Spermine.

The above results show that the group treated with RRE-1 is the most effective group on angiogenesis in both in vitro and in vivo models, and the effect of RRE-1 is superior to the effect of the clinical medication VEGF.

Experimental Example 9: Diabetic Mouse Hindlimb Ischemia Model Studies

In this study, diabetic mice were subjected to hindlimb ischemia surgery. Type 2 diabetic mice (6 in each group) were fixed on the operating table and anesthetized (1-3% isoflurane/100% oxygen at a flow rate of 1 L/min). After the mice were fixed, the areas for surgery were shaved. A 1 cm long incision was cut from the knee along the leg with a surgical knife, the incision was washed with normal saline and cotton, and then the fat tissue around the thigh muscles was removed. After the fat tissue was removed and the femoral artery was exposed, the upper and lower ends of the femoral artery were tied with 7-0 surgical suture to ensure hindlimb ischemia. Finally the wound was washed with normal saline and stitched. After the mice were recovered, they were respectively administrated with 7.8 µM nitric oxide releasing reagents (RRE-1 and VEGF), and the weights of the mice were recorded. The diabetic mice were sacrificed on the 6th and 21st day. The tissue sections of the hindlimbs were taken for immunohistochemistry (IHC). The expression of eNOS, CD31, CD34, MMP-11 and VEGFA were observed respectively. In this experiment, the mice administrated with PBS were the control group.

Figure 21:
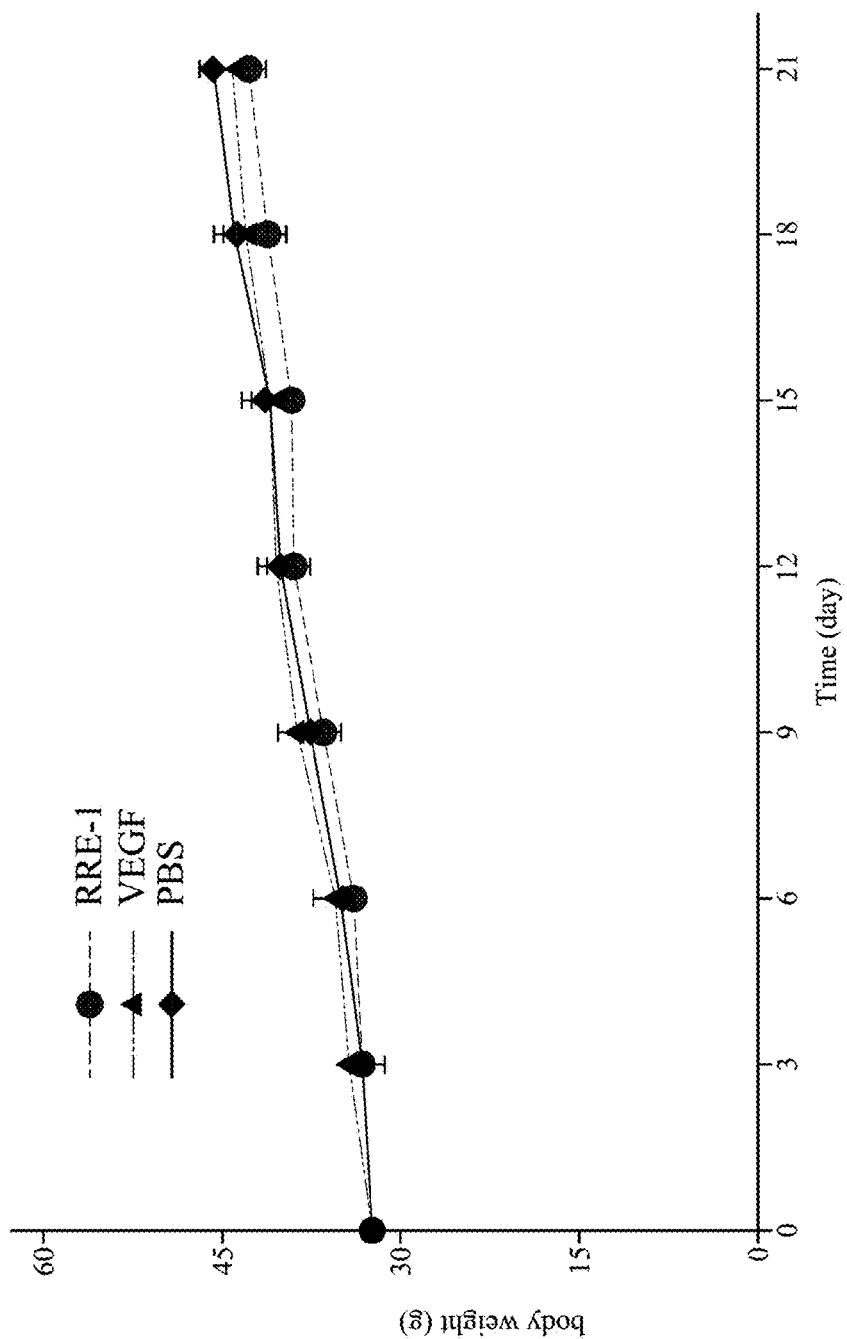
FIG. 21 shows the body weight of the mice according to an experimental example.

As shown in FIG. 21, the body weights of the diabetic mice in all three groups (RRE-1, VEGF and PBS) steadily increased during the experimental period. Further, the body weights were not different among the mice treated with different drugs. The result shows that RRE-1 had no apparent toxicity and side effects in the diabetic mice.

FIGS. 22A to 22F are histological sections stained with anti-eNOS antibodies, in which tissues in FIGS. 22A to 22C were from the ischemic hindlimbs and tissues in FIGS. 22D to 22F were from the non-ischemic hindlimbs. FIGS. 22A to 22F show that compared to administration of VEGF, administration of RRE-1 to mice promoted more eNOS expression in tissues of the ischemic hindlimb.

Please refer to FIGS. 23A to 23H, which show the IHC result of the diabetic mice with ischemic hindlimbs treated with RRE-1. The tissues in FIGS. 23A to 23D were from the ischemic hindlimb and the tissues in FIGS. 23E to 23H were from non-ischemic hindlimb.

Referring to FIGS. 24A to 24H, which show the IHC results of the diabetic mice with ischemic hindlimbs treated with VEGF. Tissues in FIGS. 24A to 24D were from the ischemic hindlimb and tissues in FIGS. 24E to 24H were from the non-ischemic hindlimb.

Referring to FIGS. 25A to 25H, which show the IHC results of the diabetic mice with ischemic hindlimbs were treated with PBS. Tissues in FIGS. 25A to 25D were from ischemic hindlimb and tissues in FIGS. 25E to 25H were from non-ischemic hindlimb.

FIGS. 23A to 23D and FIGS. 24A to 24D show that compared with the mice treated with VEGF, the mice treated with RRE-1 significantly expressed more angiogenesis-related proteins CD31, CD34, and VEGFA.

The above results show that administration of RRE-1 can effectively promote angiogenesis, the effect of RRE-1 is superior to the effect of VEGF.

From the above experimental examples of the present disclosure, RRE-1 is an effective nitric oxide releasing agent and has a better effect on cell proliferation, development of endothelial cells, promotion of wound healing, and promotion of angiogenesis.

Clinically, the selection of a nitric oxide releasing agent is tailored to the short-acting or long-acting conditions required for the pathological conditions. Taking angiogenesis as an example, it is known that different nitric oxide releasing agents have different effects on angiogenesis. For example, oxide releasing agents with shorter half-life have better effects on cell-transferring and proliferation, while those with longer half-lives have better effects on the maturation of blood vessels and angiogenesis. RRE-1 of the present disclosure is superior to other tested nitric oxide releasing agents in both cell proliferation and angiogenesis. This is because when RRE-1 was dissolved in solution or inside the animal bodies, RRE-1 can release nitric oxide more effectively, and RRE-1 had a longer duration of the capacity of releasing nitric oxide. Therefore, RRE-1 is an effective and stable nitric oxide releasing agent.

Therefore, the present disclosure provides a nitric oxide releasing compound that can directly release nitric oxide molecules and has high stability, and the rest part of the compound will not be metabolized into highly toxic molecules in vivo.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A pharmaceutical composition comprising:
a nitric oxide releasing compound of formula (I),

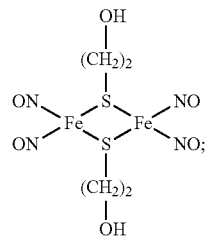

formula (I)

and
a carrying agent being water or an aqueous solution;
wherein the pharmaceutical composition is an injection formulation for a human or an animal.

2. A method of releasing nitric oxide, comprising:
administrating the pharmaceutical composition according to claim 1 to a recipient through intravenous injection, wherein the recipient is a human or an animal; and
releasing the nitric oxide from the pharmaceutical composition in the recipient.

3. The method of releasing nitric oxide according to claim 2, wherein releasing the nitric oxide in the recipient is for angiogenesis, vasodilatation, or endothelial cell proliferation.

4. A method of treating a disease in a patient, comprising:
administrating a pharmaceutical composition according to claim 1 to the patient, wherein the disease is diabetes, wounds, terminal circulation dysfunction, myocardial infarction, or stroke.

5. A method of synthesizing a nitric oxide releasing compound of formula (I),

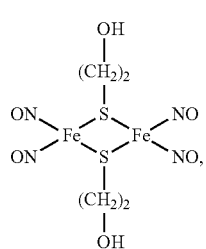

formula (I)

the method comprising:
(a) reacting iron pentacarbonyl (Fe(CO)$_5$) with sodium nitrite (NaNO$_2$) and 18-crown-6-ether to form [Fe(CO)$_3$(NO)]$^-$; and
(b) reacting [Fe(CO)$_3$(NO)]$^-$ with nitrite tetrafluoroborate (NOBF$_4$) to form an intermediate, followed by reacting the intermediate with 2-mercaptoethanol to obtain the nitric oxide releasing compound of formula (I).

6. The method of releasing nitric oxide according to claim 2, wherein the recipient has a wound, and the nitric oxide released from the pharmaceutical composition enhances healing of the wound.

\* \* \* \* \*